United States Patent [19]

Anichkov

[11] 4,230,117
[45] Oct. 28, 1980

[54] STEREOTAXIC APPARATUS

[76] Inventor: Andrei D. Anichkov, ulitsa Blokhina, 6/3, kv. 4, Leningrad, U.S.S.R.

[21] Appl. No.: 955,026

[22] Filed: Oct. 25, 1978

[30] Foreign Application Priority Data

Feb. 27, 1978 [SU] U.S.S.R. .................. 2580704

[51] Int. Cl.³ ............................................ A61B 19/00
[52] U.S. Cl. ................................ 128/303 B; 248/124; 248/285
[58] Field of Search ................. 128/303 B, 654, 754, 128/92 R, 92 A, 92 EA, 92 EB; 248/124, 222.2, 279, 285

[56] References Cited

U.S. PATENT DOCUMENTS

| | | | |
|---|---|---|---|
| 2,080,802 | 5/1937 | Anderson | 128/92 A |
| 2,519,101 | 8/1950 | Bardet | 308/6 R |
| 3,196,875 | 7/1965 | Pfeiffer | 128/303 B |
| 3,265,450 | 8/1966 | Aho | 308/6 R |
| 3,457,922 | 7/1969 | Ray | 128/303 B |

FOREIGN PATENT DOCUMENTS

| | | | |
|---|---|---|---|
| 2115121 | 10/1972 | Fed. Rep. of Germany | 128/303 B |
| 866823 | 9/1941 | France | 128/92.4 |
| 47-31591 | 8/1972 | Japan . | |
| 441933 | 12/1974 | U.S.S.R. | 128/303 B |

OTHER PUBLICATIONS

Vaskin; Proceedings of United Conference of Neurosurgeons, Nov. 11-14, 1964, Leningrad.
Laitinen, A New Stereo Encephalotome, Zentrenblatten Neurochirurgie 1971, vol. 32, H, 1-2, pp. 67-68.

*Primary Examiner*—Robert W. Michell
*Assistant Examiner*—Arthur S. Rose
*Attorney, Agent, or Firm*—Haseltine, Lake & Waters

[57] ABSTRACT

A stereotaxic apparatus comprises a ring with head clamps and an arch-shaped plate adapted to carry a stereotaxic instrument and dovably joined to a bushing by means of a guide member attached to the bushing. The bushing is mounted on a bar so as to be movable along the bar and rotable thereabout, with the bar being disposed radially relative to the arch defining the shape of the plate, and being joined to the ring by means of a spatial hinge having two degrees of freedom and mounted on the ring so as to be movable therealong. The extremity of the stereotaxic instrument is positioned at a point being the projection of the curvature center of the arch defining the shape of the plate on the axis of the bar.

2 Claims, 3 Drawing Figures

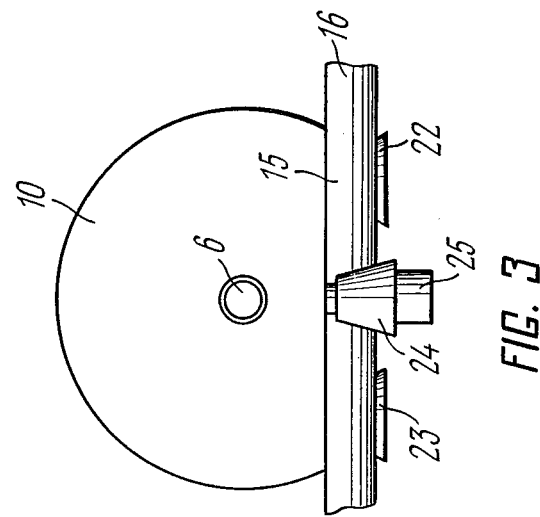
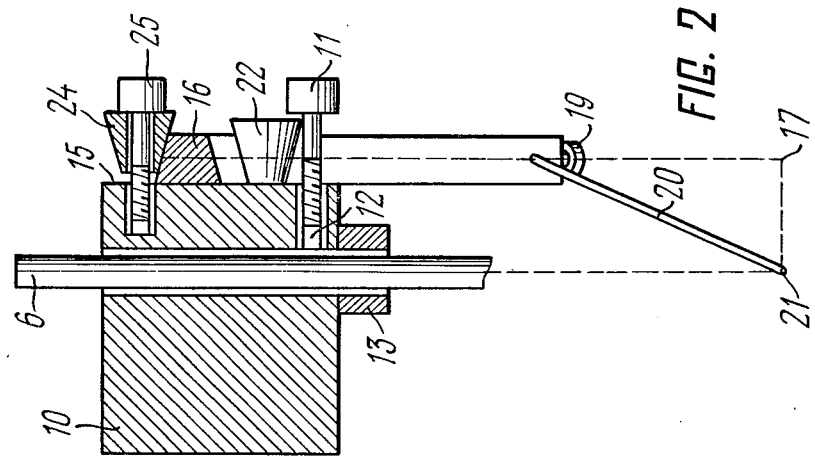

STEREOTAXIC APPARATUS

FIELD OF THE INVENTION

The present invention relates to medical instruments, and more specifically, to stereotaxic apparatus to be used in stereotaxic neurosurgery.

The best result can be achieved with the invention used in conjunction with a method disclosed in a copending application Ser. No. 945,209 filed Sept. 22, 1978, by A. D. Anichkov et al. "Method of guiding a stereotaxic instrument at an intracerebral space target point", assigned to the same applicant as the present application.

BACKGROUND OF THE INVENTION

As is known, an object of the stereotaxic operation consists in exerting influence upon a specified cerebral structure, so-called "target structure", for the purpose of producing local destructions or stimulation in this structure. A stereotaxic instrument by means of which such influence is to be exerted can be introduced to the target structure from a number of different directions. However, for every structure there are certain preferred directions enabling to preclude the possibility of serious aggravations brought about by the traumatization of vitally important centers, large blood vessels, etc. by the stereotaxic instrument. Such preferred directions and their corresponding points of surgical access located on the skull of a patient are selected on the basis of the data on the brain anatomy.

In the prior art there is known a stereotaxic apparatus /cf. Japanese Patent No. 47-31591/ which comprises a base assembly f stened to the bone edges of a trepanation apperture, and two protractors arranged in perpendicular relation to each other, the first protractor being rigidly secured to the base assembly, while the second is pivotally mounted on said first protractor and is adapted to carry a guideway with a stereotaxic instrument. Subsequent to the fixation of the stereotaxic apparatus in the trepanation aperture contrast X-ray photographic procedures and stereotaxic calculations are performed to determine the direction and depth of penetration of the stereotaxic instrument insuring its accurate contact with the target structure, whereupon the stereotaxic instrument is positioned in conformity with the resultant calculated values by employing the scales of the protractors and the scale of linear displacements provided on the guideway of the stereotaxic instrument. In this case, since the base assembly is fastened with relation to the trepanation aperture there is only one direction of penetration of the stereotaxic instrument insuring its contact with the specified target point and, consequently, the only point of surgical access to the specified structure on the surface of the cerebrum. However, this point may be located within the area of a large blood vessel where even the slightest traumatization is inadmissible.

Thus, an apparent disadvantage of the described prior art stereotaxic apparatus lies in the impossibility of changing the point of surgical access in the trepanation aperture.

Improvement of the above stereotaxic apparatus is a stereotaxic apparatus disclosed in a paper by I. S. Vaskin "New modified apparatus and needle for stereotaxic operations on the brain", Proceedings of the joint neurosurgeons' Conference, Leningrad, 1964, pp. 141-142. Similarly, this stereotaxic apparatus has a base assembly fastened to the bone edges of a trepanation apetture and comprises two protractors arranged in perpendicular relation to each other and a guideway with a stereotaxic instrument associated therewith. However the structure in question differs from the aforesaid one in that the first protractor is mounted on the base assembly so as to be movable therealong. Hence, the use of such a stereotaxic apparatus admits of altering the point of surgical access, if desired, for instance, as in the case when the point of access is located within the area of a blood vessel. To accomplish this alteration the protractors are moved along the base assembly, and then another series of contrast X-ray photographic procedures and stereotaxic calculations are performed enabling to determine a new direction of penetration of the stereotaxic instrument and, consequently, a new point of surgical access to the given target structure.

However, inasmuch as the stereotaxic apparatus is fastened with relation to the edges of the trepanation aperture, all of the potential points of surgical access are naturally to be found within the confines of this particular trepanation aperture. Yet in a number of cases a patient may have been prescribed the introduction of a stereotaxic instrument into several target structures having their points of optimum surgical access located in different areas of the cerebral surface which are lying beyond the confines of the trepanation aperture. Thus, a disadvantage inherent in the stereotaxic apparatus under consideration consists in the impossibility of localizing the points of surgical access beyond the confines of that only trepanation aperture the bone edges of which have the base assembly of the stereotaxic apparatus fastened thereto.

Also known in the prior art is a stereotaxic apparatus /cf. U.S. Pat. No. 3,357,431/ comprising a crest frame adapted to be fixed to the cranium of a patient and having a carriage movably mounted thereon and provided with a vertical strut. The vertical strut is provided with a traverse secured thereto and having arms at each of its ends adapted to carry X-ray contrast sights. The traverse has a groove to receive a stereotaxic instrument disposed movably therein, with the stereotaxic instrument and the arms being arranged in one plane, and the X-ray contrast sights and the end of the stereotaxic instrument lying along one straight line being perpendicular to the mid-sagittal plane of the patient's brain.

The spatial position of the target point relative to the stereotaxic apparatus is determined by means of contrast X-ray photography performed in two mutually perpendicular projections, and stereotaxic calculations. The carriage is moved along the plane paralled to the mid-sagittal plane of the cerebrum so as to adjust on a profile X-ray picture the projections of the X-ray contrast sights to the projection of the target point, and then the stereotaxic instrument is moved along the traverse in a straight line perpendicular to the mid-sagittal plane of the cerebrum so as to adjust on a frontal X-ray picture the projection of the stereotaxic instrument to the projection of the plane parallel to the mid-sagittal plane of the cerebrum and extending across the projection of the target point, whereafter the stereotaxic instrument is introduced into the trepanation aperture.

The stereotaxic apparatus described hereinabove furnishes surgical access to various target structures through the points on the cerebral surface which are not to be necesserily located within the confines of one trepanation aperture, but may be sufficiently spaced apart. However when employing the foregoing stereotaxic apparatus the scope of surgical access to the target structures is yet limited since with the introduction of the stereotaxic instrument into the target structure the instrument is capable of moving exclusively along the plane parallel to the mid-sagittal plane of the cerebrum. Hence, if the above stereotaxic apparatus is to be used for the purpose of stereotaxic exposure applied to the cerebral structures located in the proximity of the mid-sagittal plane, then the points of surgical access to these structures will be localized adjacent to the sagittal sinus, which is highly perilous to the patient.

Another stereotaxic apparatus known in the prior art /see T. Riechert's paper "Die stereotaktischen Hirnoperation", Deutsche Medischen Wissenschrift, 1959, vol. 84, pp. 1669–1683/ comprises a base ring with head clamps, a half-ring plate coupled to the base ring and having a carriage movably mounted thereon and adapted to hold a stereotaxic instrument. The plate has its ends attached to bushings mounted on two bars so as to be rotable thereabout. The bars are secured to the base ring in a rigidly fixed position and can be detached therefrom allowing the removal of the plate with the stereotaxic instrument from the base ring.

This stereotaxic apparatus is utilized in combination with a stereotaxic apparatus model representing an exact replica of the base ring, with a point adapted to simulate the intracerebral space target point being set forth in the stereotaxic apparatus model and its position relative to the stereotaxic apparatus being determined by means of contrast X-ray photographic procedures conducted in two mutually perpendicular, projections, and stereotaxic calculations. The adjustment of the stereotaxic instrument to the target point is effected in the following manner.

The plate with the stereotaxic instrument is mounted on the stereotaxic apparatus model fixing the bars at the locations corresponding to those at which they were secured to the base ring of the apparatus. By rotating the bushings about the bars and moving the carriage relative to the plate the stereotaxic instrument is adjusted to the point of the stereotaxic apparatus model included therein to simulate the target point, with the direction of penetration of the stereotaxic instrument being chosen in accordance with the localization of the preselected point of surgical access. Subsequently, the position of the carriage on the plate and the position of the bushings relative to the bars are fixed, the bars are detached from the stereotaxic apparatus model, the plate with the stereotaxic instrument is mounted on the base ring of the stereotaxic apparatus fastened by means of the clamps on the patient's head, and the stereotaxic instrument is introduced into the target structure through a trepanation aperture.

While using the above stereotaxic apparatus, the points of surgical access may be located both in any region of the trepanation aperture and in different trepanation apertures as well, the direction of penetration that the stereotaxic instrument is at that not limited by any planes whatsoever, in particular, by the planes parallel to the mid-sagittal plane of the cerebrum. However in those cases where prior to the introduction of the stereotaxic instrument into the target structure there arises the necessity of changing the point of surgical access, for example, due to the inaccurate performance of a trepanation aperture when one of the bone edges of the aperture prevents the stereotaxic instrument from free movement, or due to the detection of a blood vessel previously left unnoticed in the area of the point of access, the aforedescribed procedures are to be carried out once again. In doing so, the plate with the stereotaxic instrument is transferred from the base ring of the stereotaxic apparatus onto the stereotaxic apparatus model, by rotating the bushings about the bars and moving the carriage along the plate, the stereotaxic instrument is adjusted to the point of the stereotaxic apparatus model, included therein to stimulate the target point, through a new point, and a new position of the carriage and the bushings is fixed. Subsequently, the plate with the stereotaxic instrument is removed from the stereotaxic apparatus model and mounted on the base ring of the stereotaxic apparatus fastened on the patient's head. The necessity of repeating these procedures substantially increases the duration of neurosurgical intervention and the level of traumatization.

The abovementioned disadvantages are obviated in a stereotaxic apparatus /see L. Laitinen's paper "A new stereoencephalotome", Zentrenblatten Neurochirurgie, 1971, vo.. 32, H.1–2, pp. 67–68/ comprising a ring provided with head clamps and incorporating a half-ring plate mounted thereon and adapted to support a carriage with a stereotaxic instrument, with the latter being disposed radially relative to the plate. The plate has its ends rigidly attached to two bushings mounted on two hollow bars so as to be rotable thereabout and movable therealong. The bars are movably joined to the ring and can be shifted in two mutually perpendicular directions i.e. along the plane of the ring and perpendicular to this plane.

In compliance with the requirements of the X-ray photography and stereotaxic calculations the above stereotaxic apparatus is placed on the head of a patient so that the axes of the hollow bars are perpendicular to the mid-sagittal plane of the patient's brain. The position of the target point with respect to the sterotaxic apparatus is determined by means of X-ray photographic procedures and stereotaxic calculations. By shifting the bars with respect to the ring, and the bushings along the length of the bars, the half-ring periphery center of the plate is adjusted to the target point, and the positions of the bars on the ring and of the bushings on the bars resulting from such adjustment are fixed, whereupon the plate can be rotated about the bars, and the stereotaxic instrument can be moved along the plate. If the length of the stereotaxic instrument is equal to the radius of the half-ring of the plate, then the end of the stereotaxic instrument with any position of the carriage on the plate and of the plate relative to the ring will be brought into coincidence with the half-ring periphery center of the plate and, consequently, with the target point.

Thus, the foregoing stereotaxic apparatus provides the possibility of gaining surgical access to some certain target struczure through a plurality of points on the cerebral surface, while the direction of introduction of the stereotaxic instrument into the target structure is not limited by any planes whatsoever. Furthermore, in order to alter the point of surgical access there is no need for performing any additional contrast X-ray procedures, or stereotaxic calculations, or manipulations involving the transference of the plate with the stereotaxic instrument onto the stereotaxic apparatus model, since in order to accomplish this alteration it is sufficient to merely turn the bushings about the bars and/or to move the carriage with the stereotaxic instrument along the plate.

Still the stereotaxic apparatus as described above has significant disadvantages which consist in the following. The hollow bars having the bushings mounted thereon and attached to the plate are capable of moving relative to the ring only progressively in two mutually perpendicular directions. Hence, for every target point there is only one position of the bars relative to the ring insuring accurate contact of the sterotaxic instrument with this target point. The target point in this position is to be located in the straight line which is an extension of the axes of both of the hollow bars. The bars impose limitations on the movement of the carriage with the stereotaxic instrument along the plate. Due to this fact for every target structure there are two zones whence surgical access is unfeasible. Practically, when employing the above stereotaxic apparatus such limitations apply to a large area of the temporal regions wherein are located the points of access providing the shortest paths to the structures of the temporal lobes.

Moreover, turning of the plate about the bars will always be restricted in the actual conditions of the stereotaxic operation due to such hindrances as a headrest, an operating table, the trunk of a patient, etc.

Thus, a disadcantage of this prior art stereotaxic apparatus lies in the presence of the regions on the surface of the skull where surgical access to the target point is unattainable.

Further, with penetration of the stereotaxic instrument into the brain the plate made in the form of a half-ring, is positioned over the trepanation aperture and blocks the operating field interfering with the surgeon. Therefore, another disadvantage of the aforedescribed stereotaxic apparatus lies in that while using it access to the operating field is limited.

SUMMARY OF THE INVENTION

It is an object of the present invention to provide a stereotaxic apparatus insuring the expansion of surgical access to the target structure.

Another object of the present invention is to provide a stereotaxic apparatus insuring the expansion of access to the operating field.

According to the invention, the stereotaxic apparatus comprises a ring with head clamps and an arch-shaped plate adapted to carry a stereotaxic instrument and movable joined to a bushing by means of a guide attached to the bushing. The bushing is mounted on a bar so as to be movable along the bar and rotable thereabout, with the bar being disposed radially relative to the arch defining the shape of the plate, and being joined to the ring by means of a spatial hinge having two degrees of freedom and mounted on the ring so as to be movable therealong. The extremity of the stereotaxic instrument is positioned at a point being the projection of the curvature center of the arch defining the shape of the plate on the axis of the bar.

The advantages offered by the proposed stereotaxic apparatus are as follows. The possibility of moving the plate with the stereotaxic instrument about the whole periphery of the ring combined with the employment of the spatial hinge having two degrees of freedom and adapted to join the bar to the ring furnish accurate contact of the stereotaxic instrument with the target point with any position of the bar relative to the ring, when the target point is located at the axis of the bar and, consequently, from any point on the surface of the skull. The absence of another bar to provide attachment of the plate to the ring enables to achieve in the proposed stereotaxic apparatus a still further increase in the scope of access to the target point.

The movable joining of the plate to the bushing permits to diminish the overhang of the plate and thereby to obviate the abovementioned hindrances arising in the actual conditions of the stereotaxic operation on turning the plate relative to the bar. This also contributes to the expansion of surgical access to the target point.

Moreover, the cantilever arrangement of the arch-shaped plate adapted to carry the stereotaxic instrument, which is provided by joining the plate to one bar only, expands access to the operating field, since the portion of the head of a patient in the proximity of the stereotaxic instrument is, unlike the prior art apparatus described hereinabove, not overlapped by the plate.

And lastly, the proposed stereotaxic apparatus can be placed on the patient's head in an arbitrary position, i.e. disregarding any conditions concerned with the position of the elements of the stereotaxic apparatus relative to the head, which are to be satisfied, as a rule, under X-ray control when utilizing the prior art apparatus.

The arch-shaped plate may have the form of a trapezium in cross section, while the guide of the plate may be made in the form of taper rollers adapted to embrace the plate, with at least one of said rollers being mounted on the bushing so as to be mo able along the length of its axis.

Such a design of the guide permits to incorporate in the stereotaxic apparatus changeable arch-shaped plates having different radii. This provides a still further increase in the scope of access to the target point.

The foregoing and other objects as well as the advantages of the present invention will become more readily apparent on consideration of the ensuing detailed description of its preferred embodiment with reference being made to the accompanying drawings.

BRIEF DESCRIPTION OF THE DRAWINGS

FIG. 2 is a sectional view taken along line II—II in FIG. 1; and

FIG. 3 is a view taken along arrow A indicated in FIG. 1.

DESCRIPTION OF THE PREFERRED EMBODIMENT OF THE INVENTION

Figure 1:
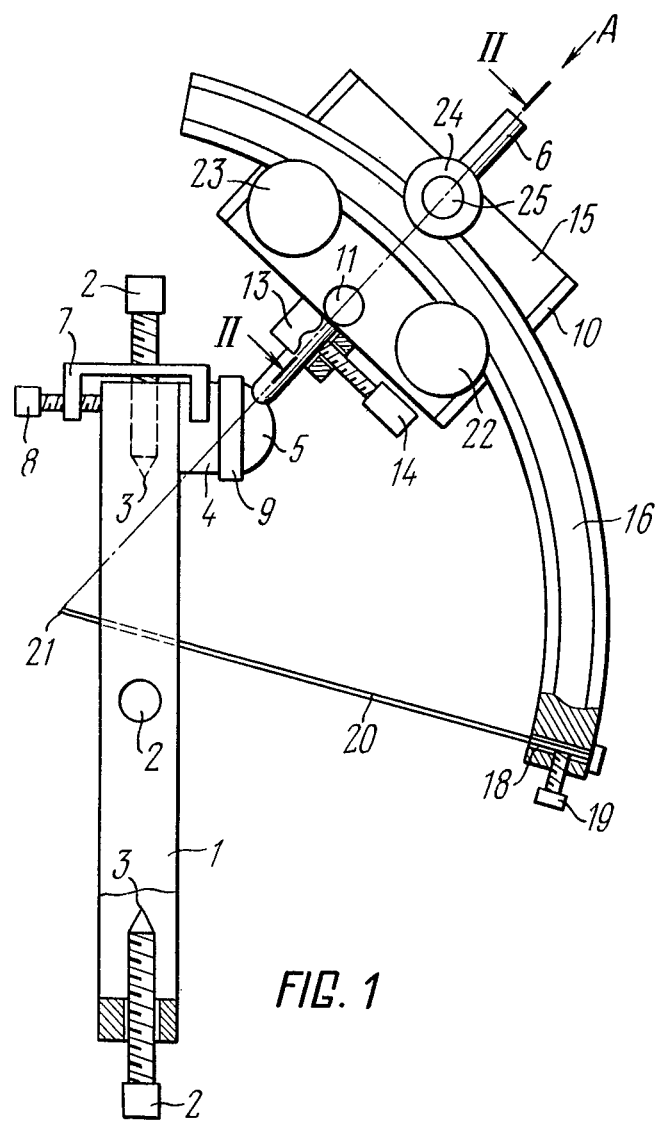
FIG. 1 is a view of a stereotaxic apparatus according to the invention.

Referring now to the drawings in more detail and in particular to FIG. 1 the stereotaxic apparatus according to the invention comprises a base ring I with threaded openings adapted to receive screws 2 each having points 3 at their ends and provided to fasten the stereotaxic apparatus onto the skull of a patient. The base ring I includes a ball-and-socket hinge mounted thereon so as to be movable about the whole periphery of the ring I and having a female portion 4 and a male portion 5. The male portion 5 of the ball-and-socket hinge has a cylindrical bar 6 attached thereto. The female portion 4 of the ball-and-socket hinge is joined to a cramping frame 7 provided with a fixing screw 8 for securing the ball-and-socket hinge to the base ring I. A nut 9 is provided for fixing the male portion 5 of the ball-and-socket hinge relative to its female portion 4 and, therefore, for fixing the position of the bar 6 on the base ring I.

To join the bar 6 to the base ring I instead of the aforesaid ball-and-socket hinge according to the invention there may be used any spatial hinge member having two degrees of freedom, insuring the possibility of rotation of the bar 6 about the axis perpendicular to the plane of the base ring I, and turning of the bar 6 about the axis parallel to the plane of the base ring I.

The bar 6 has a bushing 10 mounted thereon so as to be rotable about the bar 6 and movable therealong.

The fixing of the bushing 10 on the bar 6 is effected by driving a screw II in a threaded opening 12 /FIG. 2/ provided in the bushing 10, as a result of which the end of the screw 11 bears up against the bar 6. To restrict the movement of the bushing 10 along the length of the bar 6, yet maintaining it rotable about the bar 6, there is provided a locking ring 13 mounted on the bar 6. The position of the locking ring 13 on the bar 6 is fixed by a screw 14 /FIG. 1/ which on being driven in the respective threaded opening of the locking ring 13 bears up against the bar 6.

As best shown in FIG. 3, the cylindrical bushing 10 is cut by a plane parallel to its axis, as a result of which its lateral surface has a flat portion 15. The flat portion 15, which in FIG. 1 lies in the plane of the drawing, has an arch-shaped plate 16 abutting thereto, with the curvature center of the arch, i.e. the center of the circumference forming a part thereof, being designated by reference numerical 17. The plate 16 is arranged with respect to the bar 6 so that the axis of the bar 6 is directed radially with respect to the arch defining the shape of the plate 16, with the plate 16 being movalbe with respect to the bushing 10.

At the end of the plate 16 there is a guiding opening 18 wherein a stereotaxic instrument 20 is secured by means of a checking screw 19. The stereotaxic instrument 20 represents an electrode made in the form of a long and thin insulated needle having a non-insulated extremity 21 being the operative end of the stereotaxic instrument. As can be seen from FIG. 2, the operative end 21 of the stereotaxic instrument 20 is positioned on the axis of the bar 6 at a point corresponding to the projection of the curvature center 17 of the arch defining the shape of the plate 16 on the axis of the bar 6. Practically the length of the stereotaxic instrument 20 is approximately equal to the radius of the plate 16, since the distances from the axis of the bar 6 to the plate 16 are much less than the radius of the latter.

To join the plate 16 to the bushing 10 there is provided a guide member which, according to the specific preferred embodiment under consideration, is made in the form of three guiding taper rollers 22, 23 and 24 embracing the plate 16 /FIG. 2/ on both sides, with the plate 16 /FIG. 2/ being shaped as a trapezium in cross section, which insures the abutting of the taper rollers 22 /FIG. 1/, 23 and 24 to the plate 16 along the whole length of their forming members.

The taper rollers 22 and 23 are secured immovably onto the flat portion 15 /FIG. 3/ of the lateral surface of the bushing 10, while the taper roller 24 has an axial opening to receive a screw 25 /FIG. 2/ placed in the respective threaded opening of the bushing 16, with the roller 24 being freely rotatable about the screw 25 and movable along the length of its own axis. On driving the screw 25 in the bushing 10 the taper roller 24 presses the plate 16 to the flat portion 15 of the bushing 10 and provides, whenever required, the fixed positions of the plate 16 with respect to the bushing 10.

The guide member of the plate 16, provided for moving the plate relative to the bushing 10, may have a structural design other than that described hereinabove. The guide member may include, for example, two lugs embracing the plate 16 and concentric thereto, which are made in the form of circular segments, with one of these lugs having a threaded opening adapted to receive a checking screw providing attachment of the plate 16 to the bushing 10. The advantage of the guide member incorporating the taper rollers 22, 23 and 24 consists in that such a guide member allows for different plates having different curvature radii to be mounted thereon, thus insuring access to the target structures located at varying depths from the surface of the head. For instance, in the case where the target structure lies deep from the surface of the head, the taper rollers 22, 23 and 24 hold an arch-shaped plate having a larger radius, while the plate itself has a correspondingly longer stereotaxic instrument mounted thereon. And conversely, in the case where the target structure lies near the surface of the head, use is made of an arch-shaped plate having a smaller radius, and a shorter stereotaxic instrument. Apparently, in the latter case the taper roller 24 has to be displaced about its axis in the direction from the bushing 10.

In the embodiment shown in FIG. 1, the arch defining the shape of the plate 16 is approximately equal to 90 arc degrees. The radius of the arch amounts to about 180–200 mm. The specified dimension of the arch permits on moving the ball-and-socket hinge along the base ring I to employ any point on the surface of the head as the point of surgical access.

Although in FIG. 1 the ball-and-socket hinge with the components of the stereotaxic apparatus attached thereto is shown mounted on the upper end surface of the base ring I, it is obvious that the ball-and-socket hinge may be mounted on the lower end surface of the base ring I, providing that such a location insures optimum surgical access to the given target structure.

Prior to the beginning of the neurosurgical operation the base ring I is placed on the head of a patient and fixed by driving the screws 2 in the threaded openings of the base ring I untill the pointed ends 3 of the screws 2 thrust against the bones of the cranium. The spatial position of the target point relative to the base ring I of the stereotaxic apparatus is determined by means of contrast roentgenographic procedures combined with stereotaxic calculations. This is accomplished through the determination of the position of the base ring I with respect to some certain reference points. Such reference points may include external reference points secured to the patient's carnium, as disclosed in the copending application of A. D. Anichkov et al. "Method of guiding a stereotaxic instrument at an intracerebral space target point".

Subsequent to the determination of the position of the target point with respect to the base ring I, a model of the patient's intracerebral space is constructed by setting forth in a model of the base ring I, representing an exact copy thereof and therefore not shown in the drawings, a point adapted to simulate the target point, which is done in conformity with the resultant values of the stereotaxic calculations.

The mounting site of the ball-and-socket hinge on the base ring I is selected so as to insure optimum surgical access to the given target structure, the ball-and-socket hinge is mounted on the model of the base ring I at exactly the same location by using, for example, the scales provided on the base ring I and its model, and the cramping frame 7 is secured to the model by the screw 8. By turning the bar 6 attached to the male portion 5 of the ball-and-socket hinge and by moving 10 with the plate 16 along the bar 6, the operative end 21 of the stereotaxic instrument 20 is brought in coincidence with the point adapted to simulate the target point.

On achieving this coincidence, the position of the bar 6 with respect to the female portion 4 of the ball-and-socket hinge is fixed by the nut 9, the locking ring 13 is driven close to the bushing 10 and fixed to the bar 6 by the screw 14, whereupon the bushing 10 is made rotable about the bar 6 and the plate 16 is made movable along the taper rollers 22, 23 and 24 relative to the bushing 10. Owing to the fact that the operative end 21 /FIG.2/ of the stereotaxic instrument 20 is positioned at a point being the projection of the curvature center 17 of the arch defining the shape of the plate 16 on the axis of the bar 6, the plate 16 will be capable of moving along the surface of the sphere having its center corresponding to the point at which the operative end 21 of the instrument 20 is positioned and, consequently, the operative end 21 of the stereotaxic apparatus 20 will be brought in coincidence with the target point with any position of the plate 16 relative to the bar 6.

Then the stereotaxic instrument 20 is removed from the guiding opening 18 /FIG. 1/ or brought out therefrom in part, fixing with the screw 19. The ball-and-socket hinge is removed from the model of the base ring 1 and is secured to the base ring 1 by means of the screw 8. A trepanation aperture is performed at the chosen point of surgical access. The bushing 10 is turned about the bar 6, while the plate 16 is moved along the guiding rollers 22, 23 and 24 untill reaching the position insuring entry of the stereotaxic instrument into the trepanation aperture, whereafter the position of the bushing 10 on the bar 6 is fixed by the screw II, and the position of the plate 16 on the bushing 10 is fixed by the screw 25.

After this the stereotaxic instrument 20 is introduced into the guiding opening 18 to its full length resulting in adjustment of its operative end 21 to the target structure.

The application of the proposed stereotaxic apparatus provides the introduction of the stereotaxic instrument into the target structures through any points on the surface of the head within the area defined by the base ring as well as in the area located below the base ring. Therefore, the proposed stereotaxic apparatus is practically devoid of the limitations imposed on the selection of the point of access by the apparatus design. This enables to gain optimum surgical access for every target structure, making the stereotaxic operation less traumatic and creating the possibility of discarding the use of various specialized stereotaxic apparatus, intended, for example, for the introduction of the stereotaxic instrument only into the hypophysis. The proposed apparatus can replace all other stereotaxic apparatus, which will cut down the manufacturing and maintenance costs of the stereotaxic equipment.

Furthermore, when utilizing the proposed stereotaxic apparatus the trepanation aperture and the portion of the head in the proximity of the stereotaxic instrument are not blocked by the plate, which expands access to theoperating field. This also improves the vision of the operating field and facilitates the manipulations performed by the surgeon; hemostasis, coagulation of the cerebral membranes, etc, which results in the reduction of the duration of the stereotaxic operation.

The aforedescribed preferred embodiment of the present invention has been presented herein as merely illustrative of the spirit of the invention. It is to be understood that some variations and modifications of the above embodiment are possible without departing beyond the scope of the invention defined by the appended claims.

What is claimed is:

1. A stereotaxic apparatus comprising a ring sized to fit around the head of a patient, said ring having a plurality of head clamps, a spatial hinge having a first and a second portion, said first portion being movable with respect to said second portion through two degrees of freedom, said first portion being mounted on said ring so as to be movable therealong, an elongated bar having first and second ends, said first end being connected to said second portion of said hinge, a bushing adapted to be mounted on said bar so as to be movable therealong and rotatable thereabout, an elongated arc-shaped plate, means including a guide member of said plate for connecting said plate to said bushing so that said plate may be moved lengthwise with respect to said bushing, said bar being disposed radially with respect to an arc defining the shape of said plate, said means for connecting including means for securing said plate to said bushing, a stereotaxic instrument comprising an elongated rod having two ends, said instrument being mounted on said plate so that one end of said stereotaxic instrument is positioned at a point which is the projection of the center of curvature of the arc defining the shape of said plate on the axis of said bar.

2. A stereotaxic apparatus as recited in claim 1, wherein said plate has the form of trapezium in cross section, and said means for connecting includes taper rollers mounted on said bushing and embracing said plate, and said means for securing includes at least one of said taper rollers mounted on said bushing so as to be movable along the axis of said one roller.

* * * * *